US012728211B2

(12) United States Patent
Bosshard et al.

(10) Patent No.: US 12,728,211 B2
(45) Date of Patent: Sep. 8, 2026

(54) MECHANICAL CONTROLLING STRUCTURE FOR A DRUG DELIVERY DEVICE

(71) Applicant: Ypsomed AG, Burgdorf (CH)

(72) Inventors: Simon Martin Bosshard, Hindelbank (CH); Simon Scheurer, Bern (CH); Christian Schrul, Oberburg (CH); Martin Bruegger, Bolligen (CH)

(73) Assignee: Ypsomed AG, Burgdorf (CH)

( * ) Notice: Subject to any disclaimer, the term of this patent is extended or adjusted under 35 U.S.C. 154(b) by 385 days.

(21) Appl. No.: 18/438,094

(22) Filed: Feb. 9, 2024

(65) Prior Publication Data

US 2024/0181167 A1 Jun. 6, 2024

Related U.S. Application Data

(63) Continuation of application No. PCT/EP2022/072532, filed on Aug. 11, 2022.

(30) Foreign Application Priority Data

Aug. 13, 2021 (EP) .................................... 21191196

(51) Int. Cl.
*A61M 5/315* (2006.01)

(52) U.S. Cl.
CPC ............................... *A61M 5/31546* (2013.01)

(58) Field of Classification Search
CPC .......... A61M 5/31546; A61M 5/14248; A61M 2005/2433; A61M 5/24; A61M 2005/31588; A61M 2205/14; A61M 2005/3142; A61M 2205/6018; A61M 2205/6036; A61M 5/3135; A61M 5/2422;
(Continued)

(56) References Cited

U.S. PATENT DOCUMENTS 10,080,848 B2 9/2018 Nielsen et al.
10,188,801 B2 1/2019 Butler et al.
10,765,808 B2 9/2020 Day et al.
(Continued)

FOREIGN PATENT DOCUMENTS

EP 2637719 B1 7/2020
EP 4134114 A1 2/2023
(Continued)

OTHER PUBLICATIONS

Extended European Search Report issued in European Patent Application No. 21191196.1, mailed on Feb. 9, 2022, 6 pages.
(Continued)

*Primary Examiner* — Serkan Akar
(74) *Attorney, Agent, or Firm* — Dorsey & Whitney LLP

(57) ABSTRACT

A drug delivery device for dispensing a drug from a reservoir includes a drive unit including an electronic control circuit and a coupling portion, and a reservoir unit including the reservoir with the drug and attachable to the coupling portion. The drive unit includes a plurality of switching elements operatively coupled to the control circuit, and the reservoir unit includes at least one actuation element adapted to selectively switch at least one switching element of the plurality of switching elements when the reservoir unit is attached to the drive unit. A control signal indicative of the reservoir or the drug is generated based on the switched switching element and sent to the control circuit.

20 Claims, 3 Drawing Sheets

(58) Field of Classification Search
CPC .. A61M 2005/2407; A61M 2005/2488; A61M 2205/3561; A61M 2205/6045
See application file for complete search history.

(56) References Cited

U.S. PATENT DOCUMENTS

| | | | |
|---|---|---|---|
| 2008/0015510 | A1 | 1/2008 | Sandoz et al. |
| 2013/0131604 | A1 | 5/2013 | Avery |
| 2013/0253427 | A1 | 9/2013 | Cerman et al. |
| 2021/0038817 | A1 | 2/2021 | Carlsson et al. |

FOREIGN PATENT DOCUMENTS

| | | | |
|---|---|---|---|
| WO | 2016210404 | A1 | 12/2016 |
| WO | 2023017114 | A1 | 2/2023 |

OTHER PUBLICATIONS

International Search Report and Written Opinion issued in International Application No. PCT/EP2022/072532, mailed on Dec. 21, 2022, 8 pages.

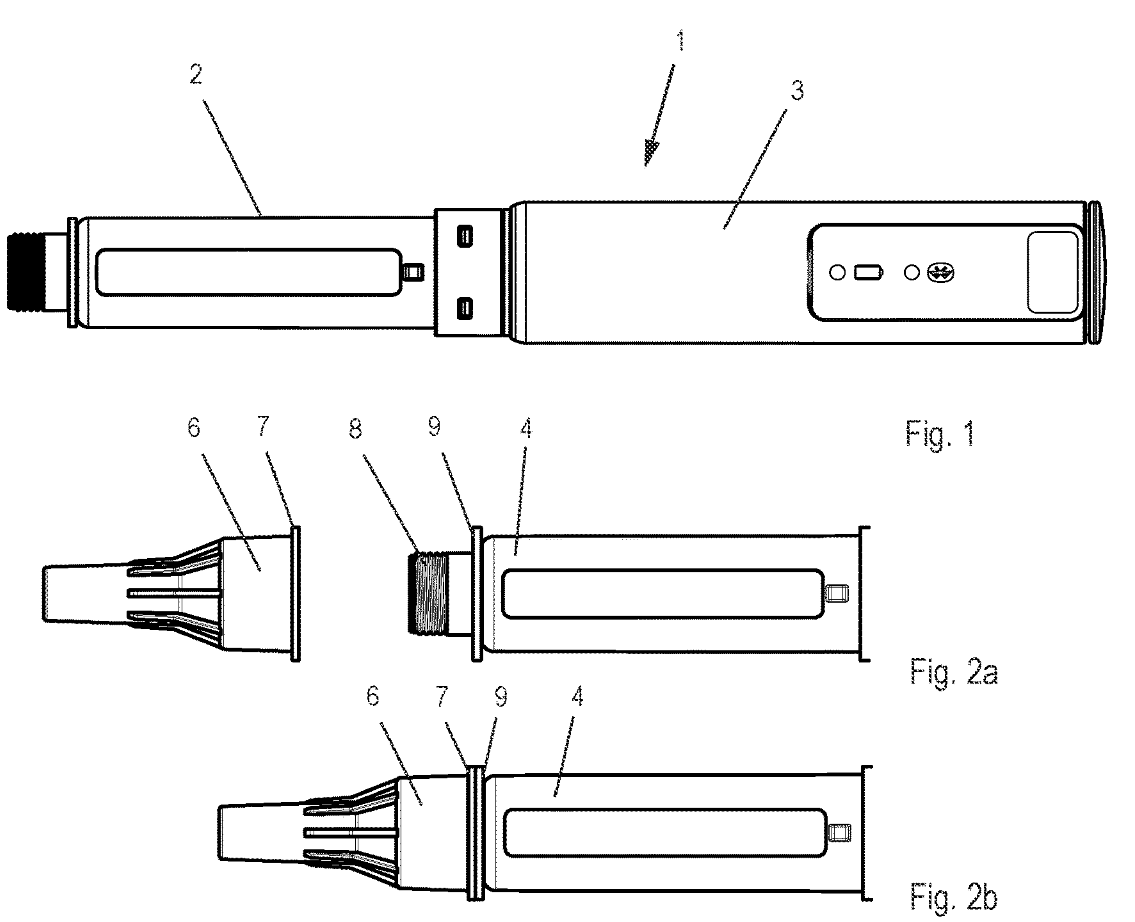
Fig. 1
Fig. 2a
Fig. 2b
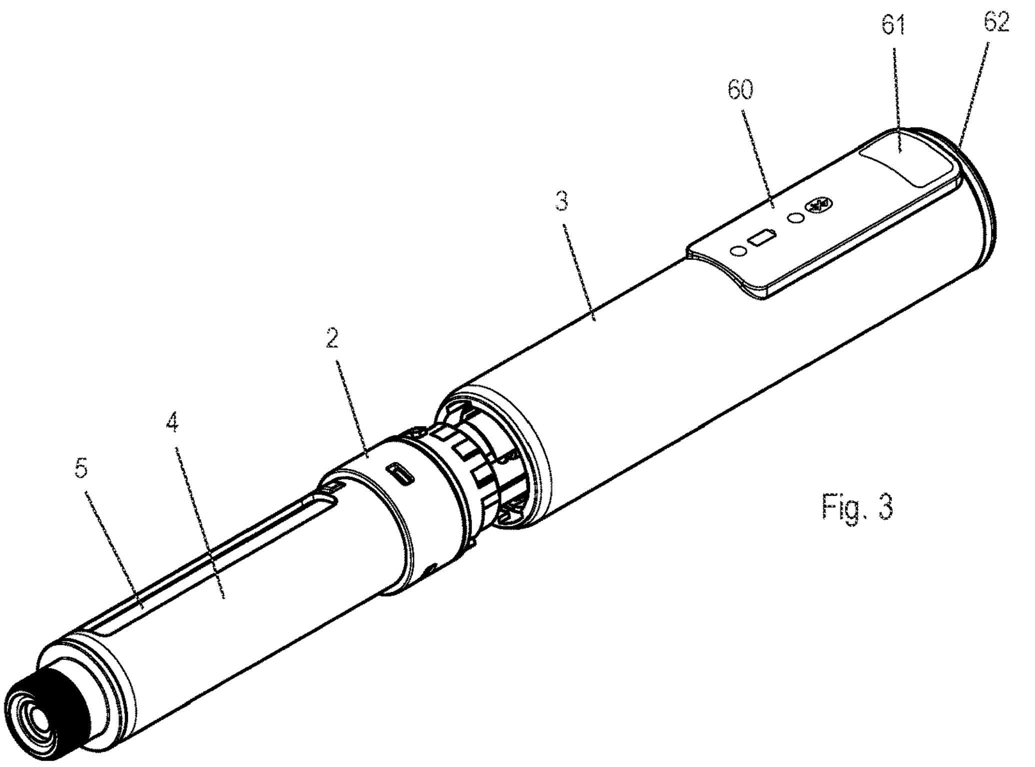
Fig. 3

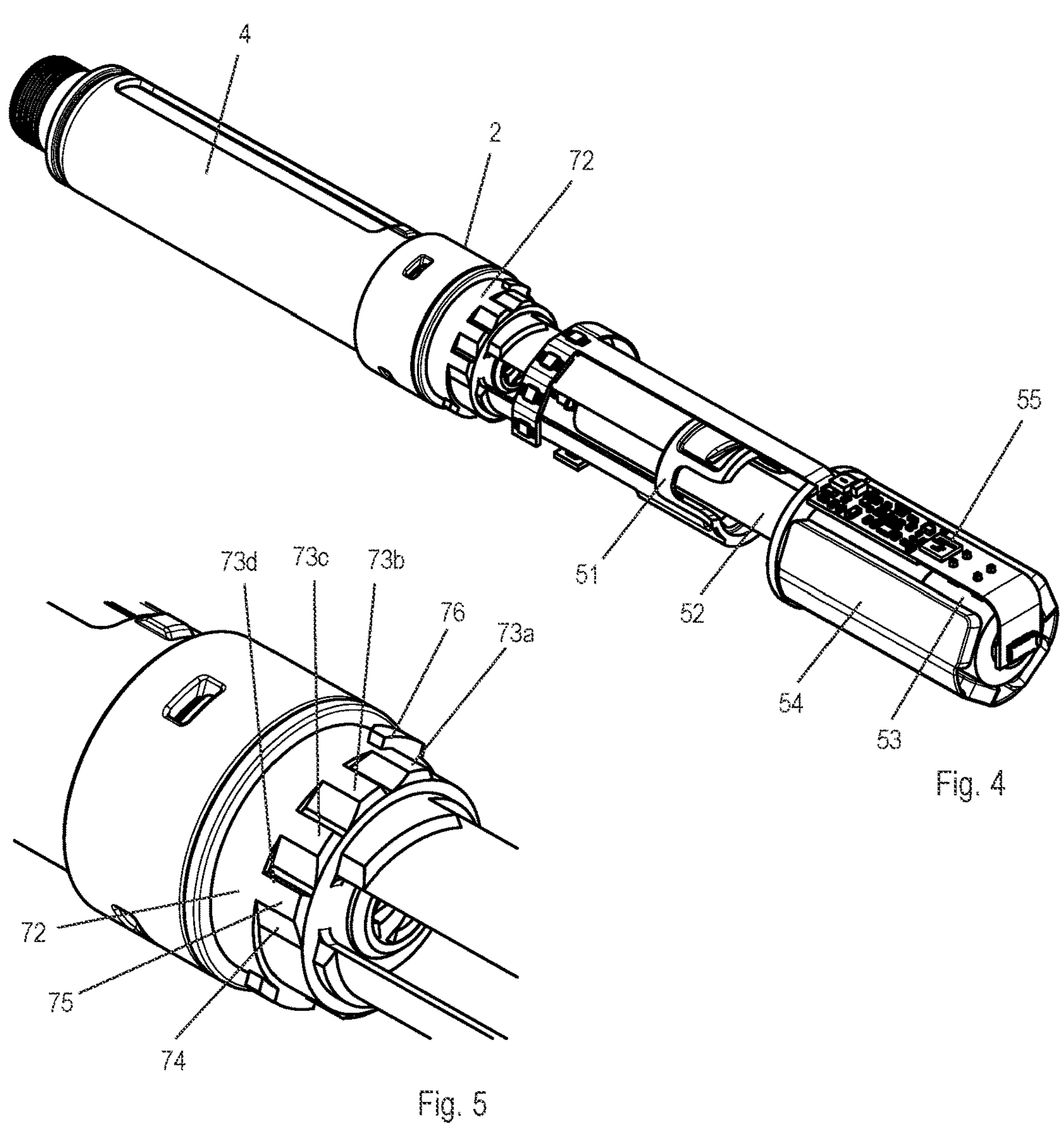
Fig. 4
Fig. 5
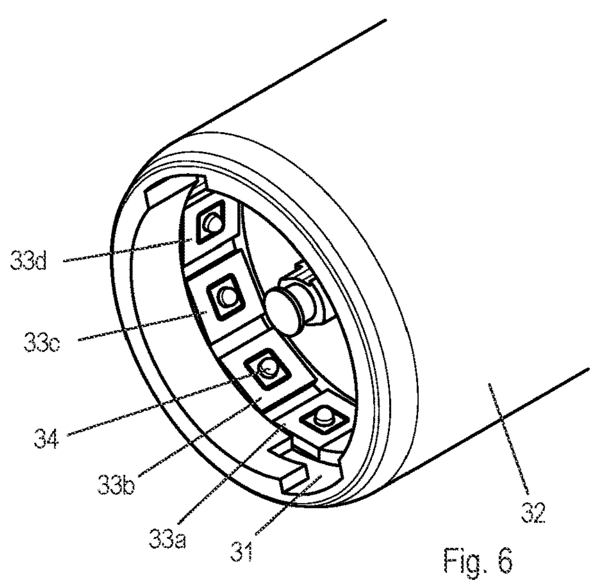
Fig. 6

33a
73a
33b
2
3
73b
33c
73c
73h
33d
33h
73d
73g
33g
73f
33f
73e
33e 3
102
33a
173a
173b
33e

MECHANICAL CONTROLLING STRUCTURE FOR A DRUG DELIVERY DEVICE

CROSS-REFERENCE TO RELATED APPLICATIONS

This application is a continuation of International Patent Application No. PCT/EP2022/072532, filed Aug. 11, 2022, entitled "MECHANICAL CONTROLLING STRUCTURE FOR A DRUG DELIVERY DEVICE", which claims priority to European Patent Application No. 21191196.1, filed Aug. 13, 2021, entitled "MECHANICAL CONTROLLING STRUCTURE FOR A DRUG DELIVERY DEVICE", each of which is incorporated by reference herein, in their entirety and for all purposes.

TECHNICAL FIELD

The present invention relates to injection devices or medicament delivery devices for injecting, delivering, administering, infusing or dispensing substances and/or liquids such as insulin, hormone preparations or vaccines. It departs from a drug delivery device comprising a drive unit including an electronic control circuit and a reservoir unit adapted to contain a reservoir with a liquid drug and attachable to the drive unit.

BACKGROUND

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process, as well as infusion devices with a cannula or needle that remains in the skin of the patient for a prolonged period of time.

By way of example, diabetes may be treated by self-administration of insulin or its derivatives with the help of multi-variable-dose insulin injection pens. An injection pen device generally has an elongate device body defining a longitudinal main device axis. An automatic injection device has a motor or a drive spring for biasing a plunger rod and shifting a piston in a container barrel, wherein the drive spring may have to be charged or strained manually prior to injection of a dose. A manually powered delivery drive requires a user to manually provide the energy to move the piston, for instance by applying a distal force component to the injection device.

The medicament dose to be injected may typically be manually selected by turning a dosage knob and observing the actual dialed dose from a dose window or display of the insulin pen. A dose is dispensed by inserting the needle into a suited portion of human skin and by moving the piston manually or by pressing a release button of an automatic injection device. Automatic injection devices may include an electronic dose dial mechanism to automatically set a dose.

Drug delivery device based therapies generally benefit from an electronic unit or control unit embedded or integrated in the delivery device, or being part of an auxiliary or supplemental electronic module or add-on device detachably attached to the delivery device. The electronic unit monitors a drug delivery process, in order to proactively prevent false handling of the device and/or to keep track of the doses already applied, and generates data related to an instantaneous condition and/or use of the delivery device. Suitable sensors of the electronic unit readily detect a status or signal from any kind of indicating component of the delivery device, including user interface elements and actuators. A wireless communication unit of the electronic unit is provided to wirelessly communicate, specifically upload, drug information to a nearby mobile device, a dedicated medical gateway or a cloud server. The drug information includes at least a time stamp and the expelled dose, indicative of a time of a medication event and of a quantity of delivered drug. The drug information may be transmitted instantaneously, or stored in a memory unit connected to the processing unit, for later upload or batch transfer.

The electronic unit may be able to detect whether or not a cartridge is inserted into the device and may read information from the cartridge by an optical sensor. In particular, devices with a replaceable cartridge may include a detection system that detects an inserted cartridge. A signal of the detection system may be transmitted to the electronic unit in the delivery device.

WO16210404 A1 discloses a cartridge module comprising standard fittings that are shared among distinct types of cartridge modules. If the cartridge module is inserted into an injector the standard fittings must be properly connected to engagement features of the injector in order for cartridge module identification code reader to successfully read the information contained in a cartridge module identification element.

EP2637719 B1 relates to a controlling of a spindle nut of a drug delivery device. When a correct cartridge assembly is attached to the delivery device, the spindle nut is prevented from rotating. Preventing rotation of the spindle allows for the spindle to move axially, and allows for dispensing of a dose. In contrast, when an incorrect cartridge assembly is attached, the spindle nut is not prevented from rotating, and this prevents dispensing of a drug. Therefore, the dispensing is only allowed for a correct cartridge assembly.

U.S. Ser. No. 10/188,801 B2 discloses to a dose setting mechanism, which locks the dose setting by preventing rotation if an incorrect cartridge is inserted and unlocks the dose setting if a correct cartridge is inserted. In an unlocked position, when a coded cartridge having a protrusion, is inserted into the drug delivery device, the protrusion pushes on a cam of a pivotable locking arm to pivot or tilt the locking arm away from a groove located in a cylindrical portion. This allows a dose setter to rotate to set a dose.

Theses prior art approaches are limited to the detection of a presence of a cartridge in the drug delivery device.

SUMMARY

It is an objective of the invention to ensure a correct handling or dispensing of a specific drug and/or a specific reservoir with a drug delivery device.

This objective is achieved by the drug delivery device and the method according to the independent claims. Preferred embodiments are evident from the dependent claims.

The present disclosure relates to a drug delivery device for dispensing a drug from a reservoir. The drug delivery device includes a drive unit including an electronic control circuit and a coupling portion, preferably at a distal end portion of a housing of the drive unit. The delivery device further includes a reservoir unit including the reservoir and/or the drug. The reservoir unit is attachable or connectable to the coupling portion of the drive unit, preferably with the proximal end portion of the reservoir unit.

The drive unit includes a plurality of switching elements in the range or area of the coupling portion. The switching elements are operatively connected to the electronic control circuit in the drive unit. The reservoir unit includes at least one actuation element or actuator adapted to selectively switch at least one of the plurality of switching elements when the reservoir unit is attached to the coupling portion of the drive unit (attached state). A control signal indicative of the reservoir and/or the drug in the reservoir unit is generated (reservoir unit specific control signal) based on the selected and switched switching element and the control signal is sent to the electronic control circuit, preferably by a detection circuit.

A predefined action or command, e.g., instruction, for the control circuit can be stored in the drive unit. Upon attachment of the reservoir unit a corresponding control signal (indicative of the reservoir and/or drug) is generated that activates or releases the predefined action or command for the control circuit. Preferably, a specific arrangement of an actuation element or/and number of actuation elements is assigned to a specific action or command. Hence, different reservoir units generate different control signals and thus reservoir unit specific actions can be carried out by control circuit.

The control signal indicative of a specific reservoir and/or specific drug is exclusively generated by the reservoir unit inside the drug delivery device. That means the drug delivery device does not need a data communication with an external device configured to send control signals to the electronic control circuit in the drive unit. Hence, the drug delivery device does not have to be connected to a network, e.g. to the internet or to a server. As the attached reservoir unit causes the switching elements to generate the control signal for the control circuit the device can be operated self-sufficiently (autarkic) and independently. However, optionally the drive unit may be configured to establish or use a data connection to an external device based on the control signal as described in detail further on.

The drive unit includes more than one mechanical or electrical switching element. At least one switching element is adapted to be switched by one or more actuation elements or actuator of the reservoir unit during attachment of the reservoir unit to the drive unit or after the reservoir unit is attached. Therefore, the plurality of switching elements allow to generate a signal that includes information beyond a simple binary state (e.g. on or off, present or not present). The plurality of switching elements may provide reservoir unit specific information such as a dose value (related to a specific drug), a priming instruction, a dispensing rate or user drug information. This information related to a specific drug. Hence, as the drive unit includes more than one switch and as the reservoir unit includes (drug related) actuation elements a reservoir unit specific (and thus drug specific) information is generated by a reservoir unit specific switching of one selected switching element or of a combination of switched switching elements. In other words, the generated signal depends on the selection and number of switched switching elements.

The switching elements may be, for example, mechanical or electrical switches. In case the switching elements are mechanical switches the actuation element may be formed as protrusion, cam, latch element or the like and adapted to abut, press or lift a member of the mechanical switch in order to actuate the mechanical switch. In case the switching elements are electrical switches the actuation member may include, for example, a conductive part, surface or portion to close or open an electric circuit of the electrical switch.

Each switching element may generate a current, or voltage signal or interrupt such a signal or close or open an electric circuit when the switching element is switched by the actuation element.

As stated above the actuation element is adapted to mechanically abut a switching element or to electrically connect a switching element. A reservoir unit may include only one or it may include a plurality of actuation elements. One actuation element may be adapted to switch one specific switching element. Alternatively, a single actuation element is adapted to switch more than one switching element. The actuation element may be arranged in a proximal portion of the reservoir unit that is adapted to be coupled with the coupling portion of the drive unit.

The drive unit is adapted to be connected to or attached to different reservoir units each including a different drug or having different properties. Besides a label or marking the reservoir unit may include a reservoir unit specific arranged actuation element and/or a specific number of actuation elements. That allows the control circuit to distinguish among different reservoir units containing, for example, different drugs, having a different size and/or different fill volume, originating from different lots and/or different manufacturer.

For example, if a first reservoir unit is attached to the drive unit that switches one or more switching elements the generated signal is different from a signal generated if a second reservoir unit (different from the first) is attached to the drive unit and one or more different switching members are switched by the second reservoir unit.

The control signal may be exploited for controlling a dispensing action or a dispensing preparation action. Examples of a dispensing action are automatically setting a dose, dispensing a dose or automatically adjusting a device set up. Examples of a dispensing preparation action are carrying out a priming step, displaying dose information to a user on a display of the drive unit or locking or unlocking a dispensing mechanism in the drive unit.

The electronic control circuit preferably includes or has access to a predefined instruction table or look-up table assigning a specific control signal to a specific action or command such as, for example, a wake-up function for the control circuit, a dose value to be set or a dispensing operation.

When the reservoir unit is attached to the drive unit at least on switch is selected and switched by at least one actuation element. The control circuit receives at least one control signal accordingly. By means of the look-up table the signal is assigned to a specific action or command and the controller carries out the defined action accordingly.

The generation of a control signal according to the present disclosure can be combined with other reservoir unit recognition means such as optical readers (optical pattern, bar code or the like on reservoir unit or on the reservoir), or near field communication means (NFC, RFID, Bluetooth) between the reservoir unit or reservoir and the drive unit. By way of example, the control circuit may receive information about the drug contained inside the attached reservoir unit from an RFID reader reading an RFID provided on an outside of the reservoir unit. Additionally, the electronic control circuits may receive information or a command for a specific dose size to be dispensed with the particular drug based on the actuation elements. The dose information is represented by the generated control signal based on the selected and switched switching elements. In this example, the reservoir unit with its arranged actuation elements may define a dose size information.

The actuation element may abut or contact the switching element to switch it if the reservoir unit is attached or connected to the drive unit. That means the switching element is switched by the actuation element when a separated reservoir unit gets into contact with the drive unit, during a connection process between the reservoir unit and the drive unit or just after the connection process when the reservoir unit is completely attached to the drive unit.

The drug delivery device may be a disposable, reusable or semi-disposable delivery device including the drive unit and the reservoir unit. The drive unit may be the reusable part of the device including a drive for moving a dispensing member such as a drive sleeve or a plunger rod in a dispensing direction in order to dispense the drug. The reservoir unit may include a reservoir holder and optionally further parts such as a pre-assembled member like the reservoir, a plunger rod, drive sleeve or/and an interface housing.

The reservoir unit may be releasably attachable to the drive unit as the reservoir unit is preferably discarded after use and the drive unit is reused for several different reservoir units. The reservoir unit may be attached to the drive unit, for example, by means of a thread, a snap-fit, a form-fit connection or a magnetic connection.

In an alternative embodiment the delivery device is a fully disposable device wherein the reservoir unit is non-releasably attachable to the drive unit. That means the reservoir unit is only used with one drive unit and the reservoir unit is attached to the drive unit during assembly of the device at the manufacturer's site or when the user carries out a final assembly step.

The drive unit includes an electronic control circuit may be adapted to control a possibly present automatic drive for dispensing the drug. Examples of such drive are a biased mechanical spring or elastic member that is released by the control circuit, an electric motor or an electromagnetic actuator such as a magnetic coil actuator. However, the automatic drive unit is not mandatory. In case the delivery device is manually operated the control circuit may be adapted to set a dose or the carry out a verification of the attached reservoir unit and configured to send information to a user based on the generated control signal.

The drive unit may include a first coupling portion at a distal end portion and the reservoir unit may include a second coupling portion at proximal end portion. Hence, the first and second coupling portions engage each other if the reservoir unit is attached, connected or coupled to the drive unit.

The actuation element may be arranged in a proximal portion of the reservoir unit. This proximal portion is adapted to be attached to the coupling portion of the drive unit. The actuation element may be adapted to switch the switching element if the reservoir unit is rotated relative to the drive unit, in particular during attachment of the reservoir unit to the drive unit. That allows an easy and reliably switching when the reservoir unit is attached or about to attach to the drive unit.

In a preferred embodiment the actuation element is arranged on an outer surface or integrally formed in an outer surface of the reservoir unit, for example, in an outer surface of a housing of the reservoir unit.

The reservoir unit may be releasably attachable to the coupling portion of the drive unit by a bayonet connection and wherein in a closed state of the bayonet connection the switching element is in a switched or actuated state. That means the switching element was switched by the actuation element during a connecting movement (e. g. establishing bayonet connection) or just at the end when the bayonet connection was completely established. In order to close the bayonet connection, the reservoir unit has to be moved relative to the drive unit wherein an axial or longitudinal movement is followed by a rotational movement. Accordingly, in order to open the bayonet connection a rotational movement is followed by a longitudinal movement of the reservoir unit relative to the drive unit.

The bayonet connection provides a safe and reliably connection between the reservoir unit and the drive unit. Furthermore, the connection is easy to establish and to release.

In a preferred embodiment the reservoir unit includes a plurality of actuation elements (e. g. forming a pattern) adapted to selectively switch switching elements when the reservoir unit is attached to the drive unit. As the drive unit includes a plurality of switching elements it is possible to switch several specifically selected switching elements. Therefore, by means of the plurality of actuation elements the corresponding generated control signal includes sophisticated information about the reservoir unit such as, for example, drug information, volume of reservoir, dose value, dispensing instructions and/or manufacturer information can be transferred to the electronic control circuit by means of selected switched switching elements.

Alternatively, the reservoir unit includes only one actuation element adapted to switch one or more selected switching element.

In a preferred embodiment the switching element is a mechanical actuation switch and the contact element is a cam. The mechanical switch may be an assembly including a housing, an actuator and a conducting path. If the actuator of the mechanical switch is depressed or otherwise moved by the cam the conducting path in an electrical switch circuit is connected or disconnected. Based on this connection or disconnection the control signal or part of the control signal can be generated.

The cam may be formed in an outer surface of a proximal portion of the reservoir unit, in particular from a housing or reservoir holder of the reservoir unit. The cam is adapted to switch the mechanical switch in a radial direction. A contact or abutment of the cam with at least one switch of the drive unit is thus ensured when the reservoir unit is attached to or is about to be attached to the drive unit.

Alternatively, the cam is formed on a proximal front end or on the proximal face of the reservoir unit. Correspondingly, the mechanical switch of the reservoir unit may be arranged on a distal front or a distally directed surface of the drive unit. In this case and in contrast to the above embodiment the cam is adapted to switch the mechanical switch in an axial direction The cam may include an inclined surface for gradual deflection of the switching element and an actuation surface rotationally or axially adjacent to the inclined surface. In other words, the cam has a ramp-shaped section and a straight outer section following the ramp section. Such a form is advantageous if the reservoir unit is rotated relative to the drive unit during attachment. The switches get into contact with the ramp or inclined surface and during rotation the switch is continuously further depressed or actuated until the actuation surface is reached. At this point the switch is fully depressed. Therefore, the inclined surface followed by an actuation surface allows to depress or activate the switch reliably and in a gently manner.

The reservoir unit is preferably inserted at least partially into an opening of a housing or holder of the drive unit when the reservoir unit is attached to the drive unit. The cam can abut or contact at least one mechanical switch of the plurality of mechanical switches which may be circumferentially arranged on an inner surface in the opening. The cam can thus easy and reliably contact the mechanical switches.

In an alternative embodiment the switching elements are electrical switches including an open circuit wherein the actuation element is an electrically conductive member adapted to close the open circuit when the reservoir unit is attached to the drive unit. Thus, the control signal is generated when the conductive member closes the open circuit of the drive unit. That means the actuation element with its conductive member and the open circuit of the drive unit form an electrical switch assembly.

The control signal represents an instruction or command for the control circuit. The control signal is preferably one of a command for activating or switch on the electronic control circuit or switch the drive unit from a power save mode to an operation mode (from sleep mode to idle mode), a command for activating a reservoir unit detection circuit, for automatically setting a dose or for driving an automatic drive of the drive unit.

By way of example, a possibly present detection circuit may be able to detect a specific reservoir unit or drug respectively based on the generated control signal. Hence, depending on the actuation element of the reservoir unit and the selected and switched switching element the control circuit is able to recognize a specific drug contained in the attached reservoir unit and/or other information related to the reservoir unit.

A specific arrangement of an actuation element or a specific arrangement of a plurality of actuation elements may represent a specific dose. For example, if a specific group of switching elements are switched the control circuit receives information for setting and displaying a specific dose for the attached reservoir unit.

The generated control signal may be, for example, an instruction or command for dispensing a single dose, a command for dispensing only a particular dose size with a specific reservoir unit or to increase the dose size over several doses (e.g. first four doses with 5 units and the following doses with 10 units).

As a further example, the control signal may represent a command for carry out a priming by an automatic drive mechanism or any other preparing step before a drug delivery process.

The drive unit may include an automatic drive and the control signal includes a dose value wherein the electronic control circuit is configured to drive the automatic drive to dispense the dose indicated in the control signal. When the user attaches the reservoir unit to the drive unit the electronic circuit receives the generated control signal with the dose information. Subsequently, the electronic circuit sets the dose. If the user starts the dispensing process, for example, by pressing a dispensing button the electronic circuit drives and controls the automatic drive (e. g. electric motor, biased drive member or electromagnetic actuator) to dispense the set dose. This may enhance the usability as the user does not have to manually set the dose. The administration of an incorrect dose caused by a wrong user input can be prevented.

The control circuit may generate a reservoir unit specific log file based on the reservoir unit specific control signal. The log file includes reservoir unit specific information such as, dispensing events (for example, time, number and size of dispensed dose), user inputs (for example, dose corrections, dose cancelling) for the specific reservoir unit and/or information about previously used reservoir units or drugs. The log file allows to collect data about user behavior, data about the use of the delivery device and/or information about occurred errors and device malfunction. The log file may be provided to an external device via a communication module in the drive unit. The external receiver may be for example a healthcare practitioner, a healthcare facility or a device or drug manufacturer.

In addition to the above mentioned self-sufficiently (autarkic) operation the drug delivery device can be operated in a connected mode. In this embodiment the control signal preferably includes a command for the control circuit to transfer automatically (e. g. without further input or user action) and wirelessly data between the drive unit and an external device. The latter may be, for example, a cloud server, an external computer of the user, a server or cloud server of a HCP, a healthcare facility or a manufacturer. That means the electronic control circuit establishes or uses a data connection between the drive unit and the external device to transmit data based on the specific reservoir unit attached to the drive unit.

For example, the control signal includes a command for the control circuit to automatically switch to a data connection mode and automatically download medication data and/or therapy data related to the previously identified (based on the reservoir unit specific control signal) medication in the attached reservoir unit. Hence, depending on the medication (or reservoir unit) the control circuit can request a medication specific look-up table and dispensing parameter from the external device.

The delivery device may be a reusable or semi-disposable injection device including the reservoir unit and the drive unit. The reservoir unit is releasably attachable to the drive unit. The reservoir unit may be replaced and discarded after an injection or if the reservoir is empty. Subsequently, a new reservoir unit may be attached to the drive unit in order to prepare the device for a new injection.

The drive unit may include an electric motor for moving a drive member in a dispensing direction to dispense the drug from the reservoir. The drug delivery device may include a reservoir or a cartridge with a one component drug inside or the drug delivery device may include a reservoir or cartridge with a two or more component drug. The latter has to be mixed by the user preferably prior an injection.

In a further embodiment the mixing of the components may be initiated if the actuation element switches the switching element. Hence, depending on the selected switched switching element the device is set into a mixing mode to prepare the drug for an administration.

Alternatively, the drug delivery device may be an infusion device such as a drug pump or a patch pump.

The switching element may be a first switching element and the drug delivery device may include further a second reservoir unit including at least a second actuation element adapted to selectively switch a second switching element when the second reservoir unit is attached to the drive unit. The second switching element is different from the first switching element. Hence, each reservoir unit attached to the drive unit forces the drive unit to generate an individual (reservoir unit specific) control signal.

If the reservoir unit includes a plurality of actuation elements the set of actuation elements of the first reservoir unit is different than a set of actuation elements of the second reservoir unit.

The present disclosure further relates to a method for generating the reservoir unit specific control command to the electronic control circuit in the drive unit of the drug delivery device. The method includes the steps of a) Attaching the reservoir unit to the coupling portion of the drive unit, by the user, preferably by means of a bayonet connection;

b) Switching of a selected switching element of the drive unit, by an actuation element of the reservoir unit during attachment;

c) Generating, by the drive unit, a control signal indicative of a reservoir and/or a drug in the reservoir unit based on the switched switching element and sending the control signal to the electronic control circuit.

The electronic control circuit may be configured to process the received control signal and determine a control command based on the control signal.

BRIEF DESCRIPTION OF THE DRAWINGS

The subject matter of the invention will be explained in more detail in the following text with reference to preferred exemplary embodiments which are illustrated in the attached drawings, in which:

FIG. 1 depicts a side view of an electronic injection pen according to the disclosure;

FIGS. 2*a* and 2*b* depict a distal end portion of the injection pen with a needle assembly;

FIG. 3 depicts a perspective view of the injection pen, wherein the reservoir unit is detached from the drive unit;

FIG. 4 depicts a perspective view of the injection pen without an outer housing of the drive unit;

FIG. 5 depicts a detail view of a proximal end portion with cams of the reservoir unit;

FIG. 6 depicts a detail view of the coupling portion with mechanical switches of the drive unit;

The reference symbols used in the drawings, and their primary meanings, are listed in summary form in the list of designations. In principle, identical parts are provided with the same reference symbols in the figures.

DETAILED DESCRIPTION

Definitions

Figures 7, 8:
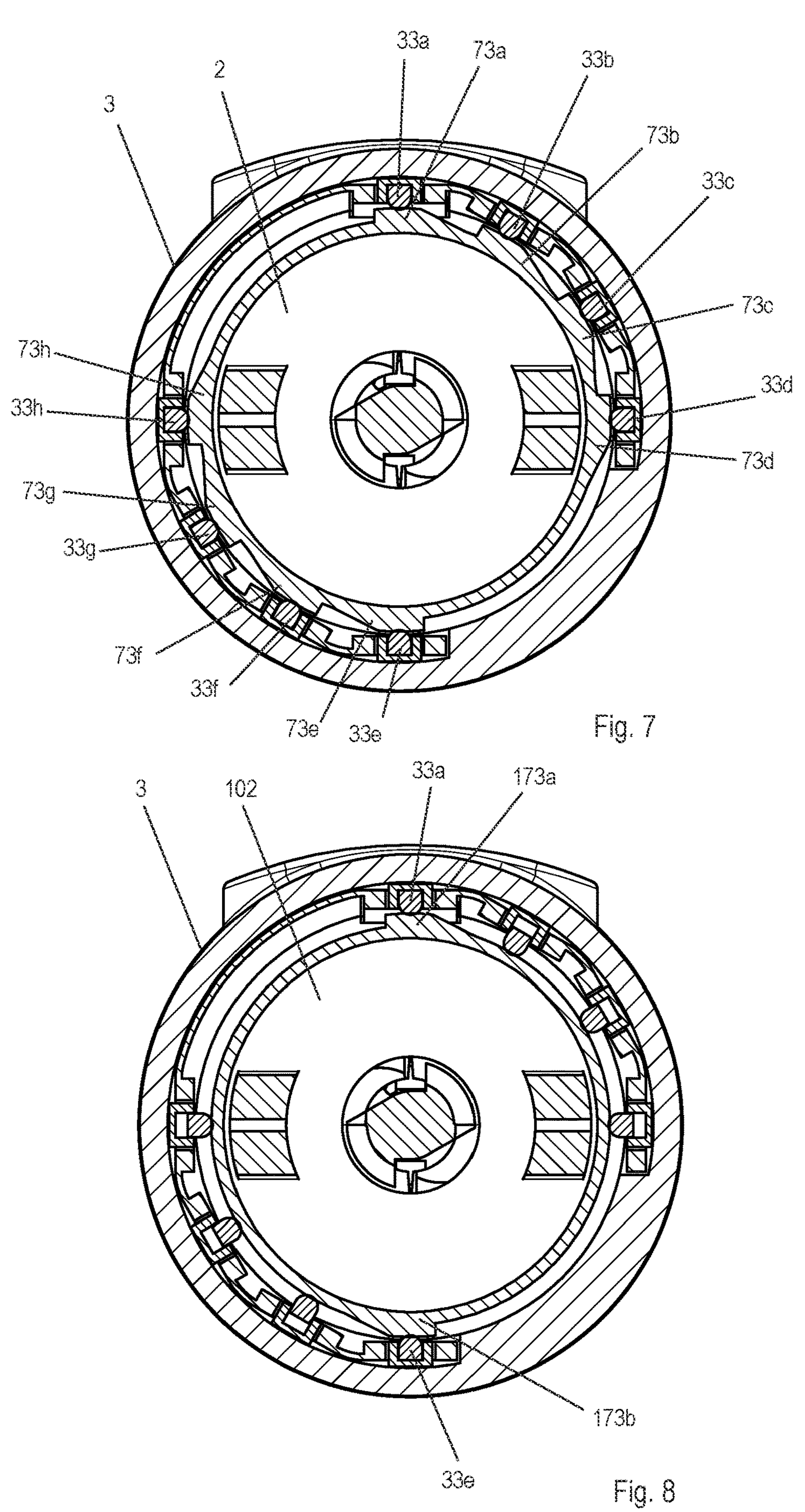
FIG. 7 depicts a sectional view with a cut through in a plane perpendicular to the longitudinal axis of the injection pen and FIG. 8 depicts a sectional view of a second embodiment.

In the present description the term "distal" refers to the side where the needle is attached. This is on the left hand side in the FIGS. 1 to 6. The term "proximal" refers to the opposite side furthest away from the needle side (right hand side in FIGS. 1 to 6).

In the present context, the terms "substance", "drug", "medicament" and "medication" are to be understood to include any flowable medical formulation suitable for controlled administration through a means such as, for example, a cannula or a hollow needle, and includes a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances The term "injection system" or "injector" refers to a device that is removed from the injection site after each medication event or drug delivery process, whereas the term "infusion system" refers to a device with a cannula or needle that remains in the skin of the patient for a prolonged period of time, for example, several hours.

FIG. 1 shows a side view of a drug delivery device according to the present disclosure. In the embodiment shown in FIG. 1 the device is implemented as a semi-disposable electronic injection pen 1. The injection pen 1 includes a disposable assembly or reservoir unit 2 and a reusable assembly or drive unit 3.

FIGS. 2*a* and 2*b* depict a distal portion of a reservoir holder 4 of the injection pen 1. As shown in FIG. 2*a* the reservoir holder 4 includes a cylindrical portion including a thread 8 on the outside of the cylinder on its distal end. On a proximal end of the cylinder portion is a circumferential collar 9 or rim portion arranged. The collar 9 is adapted to support a needle assembly 6 by supporting a proximal rim 7 of a housing of the needle assembly 6.

As shown in FIG. 2*b* the needle assembly 6 can be mounted, namely clipped-on the thread 8 of the reservoir holder 4. As the collar 9 circumferentially supports the proximal rim 7 of the needle assembly 6 the mounting of the needle assembly 6 is facilitated. The user can insert the thread 8 into the housing of the needle assembly 6 until the proximal rim 7 abuts the distal surface of the collar 9. When the rim 7 contacts the collar 9 the user knows that the needle assembly 6 is fully inserted and correctly mounted to the reservoir holder 4. Hence, the collar 9 of the reservoir holder 4 provides a visual indicator or reference element for the user during mounting the needle assembly 6.

Furthermore, the collar 9 prevents the mounted needle assembly 6 from tipping to one side and thus ensures that the needle assembly 6 is hold in place relative to the reservoir holder 4.

FIG. 3 depicts a perspective view of the injection pen 1 of FIG. 1 wherein the reservoir unit 2 is detached from the drive unit 3. The reservoir unit 2 includes the reservoir holder 4 and a reservoir in form of a cartridge 5 containing liquid drug. The drive unit 3 includes an automatic drive, a dispensing button 62 and a LCD unit 60 with a display 61. The drive unit 3 is releasably attachable to the reservoir unit 2 by a bayonet connection.

The reservoir unit 2 can be produced, pre-assembled and stored separately from the reusable assembly 3. That is, single parts of the reservoir unit 2 may be produced by a device manufacturer and delivered to the drug or medication manufacturer. The latter inserts the filled cartridge in the reservoir holder and pre-assembles the single components to the sub-assembled reservoir unit 2.

FIG. 4 depicts a perspective view of the injection pen. An outer housing of the drive unit 3 is not shown in order to show the elements inside the drive unit 3. The drive unit 3 includes a support structure 51 an electric motor 53, in particular a brushless DC (BLDC) motor or stepper motor, for moving a plunger rod, a sleeve-shaped automatic drive member 52, a gear connecting a motor shaft to the automatic drive member 52, a printed circuit board (PCB) 55 with an electronic control circuit and a controller for controlling the electric motor 53, an energy source in form of a rechargeable battery 54, a NFC reader, a data storage module, a communication module (on the PCB 55) and an encoder for sensing the movement of the motor shaft.

In an alternative embodiment the automatic drive unit may not include any display but only simple LEDs or no indication means at all. In this case the data are transmitted from the drive unit to a user device with a display for displaying the information.

The reservoir unit 2 includes at least an interface housing 72, the reservoir holder 4, the cartridge 5, a flange and the plunger rod. A pen cap can be mounted on the reservoir holder 4. On an outside of the interface housing 72 a NFC tag including information of the drug is optionally arranged.

As best shown in FIG. 5, which depicts a detail of the proximal end portion of the reservoir unit 2, the interface housing 72 includes in a proximal portion circumferentially arranged actuation elements in form of cams 73*a*-73*d* (cams 73*c*-73*h* shown in FIG. 7). The cams 73*a*-73*h* are integrally formed in an outer surface of the interface housing 72. As shown in FIG. 5 each cam 73*a*-73*h* includes an inclined surface 74 and an actuation surface 75 adjacent to the inclined surface 74. The cams 73*a*-73*h* have thus a ramp-shape or saw tooth-shape. Furthermore, the interface housing 72 includes two opposite arranged protrusions 76 adapted to engage into corresponding nuts 31 in the housing 32 of the drive unit 3. As it can be seen in FIG. 6 the nut 31 is L-shaped and includes an axial portion and a circumferential portion in order to enable a bayonet connection when the protrusion 73 is inserted into the nut 31. The location, size and number of cams 73 may differ among different reservoir units as described below with respect to FIGS. 7 and 8.

FIG. 6 depicts a detailed view of a distal end portion or coupling portion of the drive unit 3. In this end portion the drive unit 3 includes mechanical switches 33*a*-33*d* (switches 33*e*-33*h* shown in FIG. 7) inside an opening of the housing 32 and circumferentially positioned therein. Each mechanical switch 33*a*-33*h* includes a contact surface 34 and a conductive path that is part of an electrical circuit. When one of the cams 73*a*-73*h* comes into contact and presses on the contact surface 34 of one of the switches 33*a*-33*h* the electric switch circuit is closed and a control signal is generated. The switches 33*a*-33*h* are electrically connected to the PCB 55 (see FIG. 4) and hence to the controller.

To attach the reservoir unit 2 to the drive unit 3 the user inserts the proximal portion of the interface housing 72 of the reservoir unit 2 into the opening in the housing 32 of the drive unit 3 until a ledge of the interface 72 housing abuts a distal rim of the housing 32. During this step the protrusions 76 are inserted into the axial portion of the L-shaped nuts 31 in the housing 32. During this axial movement of the reservoir unit 72 relative to the drive unit 3 the cams 73*a*-73*h* enter a space between two adjacent switches 33*a*-33*h* without contacting the switches 33*a*-33*h*.

To establish and close the bayonet connection and thus to completely attach the reservoir unit 2 to the drive unit 3 the reservoir unit 2 is rotated relative to the housing 32 until a stop position is reached. When starting the rotational movement the protrusions 76 enter the circumferential position of the L-shaped nuts 31. At the same time the contact surfaces 34 of the switches 33*a*-33*h* get into contact with the inclined surfaces 74 of the cams 73*a*-73*h*. When the reservoir unit 2 is further rotated the inclined surfaces 74 further presses the contact surfaces 34 down and the switches 33*a*-33*h* come into contact with the actuation surface 75 and the switches are switched.

After completing the rotational movement the reservoir unit 2 is mechanically coupled to the drive unit 3 by the bayonet connection. Additionally, the actuation surfaces 75 of the cams 73*a*-73*h* is located on the contact surfaces 34 of the switches 33*a*-33*h* and thus keep the switches 33*a*-33*h* pressed and activated. In this attached state the switches 33*a*-33*h* selectively switched by the cams 73*a*-73*h* generate a control signal for the controller in the drive unit 3.

In this embodiment all switches 33*a*-33*h* are selected and switched. However, this depends on the attached reservoir unit. As it will be apparent from the second embodiment the drive unit 3 is adapted to be connected to different types of reservoir units having a different arrangement of cams and not all switches 33*a*-33*h* may be switched. Hence, the drive unit 3 generates an individual control signal for each different reservoir unit.

To release and detach the reservoir unit 2 form the drive unit 3 the reservoir unit 2 is rotated in reverse direction. By this the cam 73*a*-73*h* get out of engagement with the switches 33*a*-73*h*. After the reverse rotation the reservoir unit 2 can be moved axially away from the housing 32. The protrusions 76 move out of the L-shaped nuts 31 and the reservoir unit 2 can be completely separated from the drive unit 3.

FIGS. 7 and 8 depicts a sectional view where the cut runs through the injection pen 1 in a plane perpendicular to the longitudinal axis of the device.

FIG. 7 depicts an attached state with a first reservoir unit 2. As shown in FIG. 7 the interface housing 72 of the first reservoir unit 2 includes eight cams 73*a*-73*h* in total that switch all eight mechanical switches 33*a*-33*h* of the drive unit 3, when the first reservoir unit 2 is attached to the drive unit 3.

In contrast, in FIG. 8 a second reservoir unit 102 (different from the first) is attached to the same drive unit 2. The interface housing 172 of the second reservoir unit 102 includes only two cams 173*a*, 173*b* oppositely arranged to each other. Consequently, only two mechanical switches 33*a*, 33*e* of total eight switches 33*a*-33*h* of the drive unit 3 are switched. Therefore, the control signal generated by the switched switches 33*a*-33*h* of the first reservoir unit 2 is different than the control signal generated by the two switches 33*a*, 33*e* switched by the cams 173*a*, 173*b* of the second reservoir unit 102.

The drive unit 3 includes a memory including a look-up table. Each possible selection or combination of switched switches is associated with a specific instruction, action or command for the controller. Hence, if the controller receives the signal from the switched switches, the controller determines based on the look-up table the information, action or command that is associated to the specific control signal.

By way of example, in the following use case with the present disclosure is described.

When a reservoir unit with a liquid drug was attached to the drive unit as described above the switch circuits of the actuated switches are closed and generate a control signal to the controller (to the electronic control circuit). Hence, the controller receives a control signal based on the mechanical switches that were selectively actuated by the cams of the reservoir unit.

In this example the selected combination of switched switches generates a control signal that is assigned to a command for instructing or causing the controller to activate the controller and switch the circuit from power off to power on or from a sleep mode to an activate mode, to carry out a priming and to set a dose value to be dispensed. Optionally, the control signal may include a command for the controller to automatically establish a wireless data connection to a cloud server and to download drug specific dose information from a user therapy plan.

Optionally, before the controller can start a dispensing operation a verification of the drug has to be done. For this purpose the code reader of the drive unit reads the NFC tag on the reservoir unit. The controller verifies with an internal or external database (data connection) if the drug has not been expired and/or if the drug is in line with a user specific therapy plan. In case the predefined requirements are met the controller drives the electric motor in a priming mode and moves the drive member and plunger rod a short distance in dispensing direction to prime the system. Subsequently, the dose value provided in the control signal and determine based on the look-up table is set. The set dose is displayed on the LCD. When the users presses the dose knob the controller starts to drive the motor to dispense the set dose.

While the invention has been described in detail in the drawings and foregoing description, such description is to be considered illustrative or exemplary and not restrictive. Variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF REFERENCE NUMBERS

1 Injection pen
2, 102 Reservoir unit
3 Drive unit
4 reservoir holder
5 Cartridge
6 needle assembly
7 proximal rim
8 thread
9 collar
31 nut
32 housing
33*a*-33*h* mechanical switch
34 contact surface
51 supporting structure
52 drive member
53 electric motor
54 battery
55 PCB
60 display unit
61 LCD
72 interface housing
73*a*-73*h* cam
173*a*, 173*b* cam
74 inclined surface
75 actuation surface
76 protrusion

What is claimed is:

1. A drug delivery device for dispensing a drug from a reservoir, the device comprising:

a drive unit comprising an electronic control circuit and a coupling portion; and a reservoir unit comprising the reservoir and/or the drug, wherein the reservoir unit is attachable to the coupling portion, wherein the drive unit comprises a plurality of switching elements operatively coupled to the control circuit, and the reservoir unit comprises at least one actuation element adapted to selectively switch at least one switching element of the plurality of switching elements when the reservoir unit is attached to the drive unit, wherein the at least one actuation element is arranged in a proximal portion of the reservoir unit and adapted to be attached to the coupling portion, and the at least one actuation element is adapted to switch the at least one switching element when the reservoir unit is rotated relative to the drive unit, and wherein a control signal is generated based on a selection of and a number of switched switching elements of the plurality of switching elements, and the control signal is sent to the control circuit and comprises an instruction for driving an automatic drive of the drive unit or for automatically setting a dose.

2. The drug delivery device according to claim 1, wherein the reservoir unit is releasably attachable to the coupling portion by a bayonet connection, and wherein in a closed state of the bayonet connection, the switching element has been switched by the at least one actuation element.

3. The drug delivery device according to claim 1, wherein the reservoir unit comprises a plurality of actuation elements adapted to selectively switch the plurality of switching elements when the reservoir unit is attached to the drive unit.

4. The drug delivery device according to claim 1, wherein the plurality of switching elements are mechanical switches and the at least one actuation element is a cam.

5. The drug delivery device according to claim 4, wherein the cam is formed in an outer surface of a proximal portion of the reservoir unit.

6. The drug delivery device according to claim 4, wherein the mechanical switches are circumferentially arranged inside an opening of the drive unit.

7. The drug delivery device according to claim 1, wherein the plurality of switching elements comprise electrical switches including an open circuit, wherein the at least one actuation element is an electrically conductive member adapted to close the open circuit if the reservoir unit is attached to the drive unit.

8. The drug delivery device according to claim 1, wherein the control signal further comprises one or more of an instruction for activating the electronic control circuit, an instruction for activating reservoir unit detection means, or an instruction for carrying out a priming by the automatic drive mechanism.

9. The drug delivery device according to claim 1, wherein the control signal comprises a dose value, and wherein the electronic control circuit is configured to drive the automatic drive to dispense the dose based on the control signal.

10. The drug delivery device according to claim 1, wherein the control circuit is configured to generate a reservoir unit specific log file based on the control signal and to store data related to drug delivery events of the reservoir unit.

11. The drug delivery device according to claim 1, wherein the control signal comprises an instruction for the control circuit to automatically transfer data between the drive unit and an external device.

12. A drug delivery system comprising the drug delivery device according to claim 1, wherein the at least one switching element is a first switching element, and further comprising a second reservoir unit, the second reservoir unit comprising at least a second actuation element configured to selectively switch a second switching element of the plurality of switching elements, different from the first switching element, when the second reservoir unit is attached to the drive unit.

13. A method of generating a reservoir unit specific control command for the electronic control circuit in the drive unit of the drug delivery device of claim 1, the method comprising the steps of:

a) attaching the reservoir unit to the coupling portion of the drive unit;

b) switching of the at least one switching element of the plurality of switching elements of the drive unit by the actuation element of the reservoir unit during the step of attaching; and c) generating, by the drive unit, the control signal indicative of a reservoir and/or a drug in the reservoir unit based on the step of switching of the at least one switching element and sending the control signal to the electronic control circuit.

14. A drug delivery device for dispensing a drug from a reservoir, the device comprising:

a drive unit comprising an electronic control circuit and a coupling portion; and a reservoir unit comprising the reservoir and/or the drug, wherein the reservoir unit is attachable to the coupling portion, wherein the drive unit comprises a plurality of switching elements operatively coupled to the control circuit, and the reservoir unit comprises at least one actuation element adapted to selectively switch at least one switching element of the plurality of switching elements when the reservoir unit is attached to the drive unit, wherein the plurality of switching elements are mechanical switches and the at least one actuation element is a cam formed in an outer surface of a proximal portion of the reservoir unit, the cam comprising an inclined surface for gradual deflection of a corresponding switching element and an actuation surface adjacent to the inclined surface for maintaining the corresponding switching element in a switched state, and wherein a control signal is generated based on a selection of and a number of switched switching elements of the plurality of switching elements, and the control signal is sent to the control circuit and comprises an instruction for driving an automatic drive of the drive unit or for automatically setting a dose.

15. The drug delivery device according to claim 14, wherein the reservoir unit is releasably attachable to the coupling portion by a bayonet connection, and wherein in a closed state of the bayonet connection, the switching element has been switched by the at least one actuation element.

16. The drug delivery device according to claim 14, wherein the reservoir unit comprises a plurality of actuation elements adapted to selectively switch the plurality of switching elements when the reservoir unit is attached to the drive unit.

17. The drug delivery device according to claim 14, wherein the mechanical switches are circumferentially arranged inside an opening of the drive unit.

18. The drug delivery device according to claim 14, wherein the plurality of switching elements comprise electrical switches including an open circuit, wherein the at least one actuation element is an electrically conductive member adapted to close the open circuit if the reservoir unit is attached to the drive unit.

19. The drug delivery device according to claim 14, wherein the control signal comprises an instruction for the control circuit to automatically transfer data between the drive unit and an external device.

20. A drug delivery system comprising the drug delivery device according to claim 14, wherein the at least one switching element is a first switching element, and further comprising a second reservoir unit, the second reservoir unit comprising at least a second actuation element configured to selectively switch a second switching element of the plurality of switching elements, different from the first switching element, when the second reservoir unit is attached to the drive unit.

* * * * *